(12) United States Patent
Luizzi, Jr. et al.

(10) Patent No.: US 6,595,977 B1
(45) Date of Patent: Jul. 22, 2003

(54) ABSORBENT ARTICLE HAVING A HIGH COEFFICIENT OF FRICTION BACKSHEET AND A SELF-RELEASE TAPE TAB

(75) Inventors: Joseph Michael Luizzi, Jr., Newton, PA (US); Miriam Motta, Franklin Park, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/553,576

(22) Filed: Apr. 20, 2000

(51) Int. Cl.[7] .............................................. A61F 13/15
(52) U.S. Cl. ............ 604/390; 604/385.02; 604/385.03; 604/385.04; 604/385.05
(58) Field of Search ................. 604/385.02, 385.03, 604/385.04, 385.05, 385.14, 385.22, 386, 387, 390; 206/438, 440

(56) References Cited

U.S. PATENT DOCUMENTS

| | | | | |
|---|---|---|---|---|
| 3,888,255 A | * | 6/1975 | Shah et al. ............. 128/290 R |
| 4,850,991 A | * | 7/1989 | Nakamishi et al. ......... 604/387 |
| 5,011,480 A | | 4/1991 | Gossens et al. |
| 5,217,448 A | | 6/1993 | Glaug et al. |
| 5,591,147 A | * | 1/1997 | Couture-Dorschner et al. .. 604/369 |
| 5,993,430 A | * | 11/1999 | Gossens et al. .......... 604/385.1 |
| 6,063,065 A | * | 5/2000 | Costa ....................... 604/385.1 |
| 6,365,794 B1 | * | 4/2002 | Dabi et al. ................. 604/367 |
| 6,508,795 B1 | * | 1/2003 | Samuelsson et al. ....... 604/378 |
| 6,524,289 B1 | * | 2/2003 | Larsson et al. ........ 604/385.01 |

FOREIGN PATENT DOCUMENTS

JP          05103812 A * 4/1993 ........... A61F/13/14

* cited by examiner

*Primary Examiner*—Weilun Lo
*Assistant Examiner*—Michael G Bogart

(57) ABSTRACT

The present invention relates to an absorbent article for managing bodily fluids, comprising a high coefficient of friction ("COF") backsheet and at least one tape tab extending therefrom. The tape tab comprises a minimum amount of pressure sensitive adhesive sufficient to maintain the position of the article when a user's undergarments are away from her body. When the undergarments are near her body, the high COF backsheet acts as the predominant means for maintaining the position of the article due to normal forces exerted by the user's body and undergarments. When the user wants to remove the article from her undergarments, the tape tab provides additional advantages. The user may grasp the tape tab itself for removing the article as an alternative to grasping a portion of the soiled article. In addition the soiled article may be folded or rolled up, and then held in that configuration with the tape tab, for convenient and discreet disposal.

7 Claims, 3 Drawing Sheets

ABSORBENT ARTICLE HAVING A HIGH COEFFICIENT OF FRICTION BACKSHEET AND A SELF-RELEASE TAPE TAB

FIELD OF THE INVENTION

The present invention relates to an absorbent article having a substantially tack free, high coefficient of friction backsheet for holding the article in place during use, and at least one self-release tape tab for positioning the article in a user's undergarments and maintaining its position in the absence of any exerted normal force on the article. Absorbent articles of the present invention include sanitary napkins, pantiliners, incontinence devices, diapers, and the like.

BACKGROUND OF THE INVENTION

Many absorbent articles, especially those designed and configured to absorb vaginal and/or urethral discharge, utilize pressure sensitive positioning adhesive on a backsheet layer to attach the article to a user's undergarment. To protect the positioning adhesive prior to use, a releasable sheet is typically applied over the adhesive. Disadvantages accompanying the use of a release sheet and positioning adhesive are numerous; some of which are illustrated below.

Release sheets are typically constructed from silicone coated paper, accounting for an expensive component in an absorbent article's composition. Moreover, consumers find it inconvenient and indiscreet to dispose of the sheet after removing it from the article.

One approach proposed for eliminating the need for a separate release sheet is to apply a release coating to a film overwrapper and adhere the article directly to the overwrapper. This approach eliminates some of the cost of a release sheet, but maintains the most expensive component, the coating itself. Another disadvantage of this approach is the requirement of an overwrapper. Many commercially available absorbent articles are sold in cartons or bags, and are thus not individually packaged with overwrappers.

U.S. Pat. No. 5,217,448 discloses an absorbent product having optional side panel usage. The products have side flaps with adhesive thereon and corresponding release areas on the undergarment-facing side of the product for the flaps to releasably adhere to. This configuration eliminates the need for a release sheet to protect the flap adhesive. The flaps can optionally be removed from the release area and attached to a user's undergarment. Additional zones of pressure sensitive adhesive occupy the undergarment-facing side of the article for maintaining the product's position during use, especially when the flaps are not employed. However, zones of positioning adhesive present other disadvantages. Portions of the positioning adhesive may remain in a user's undergarment after removing the absorbent article, creating the potential for the remaining adhesive to come into contact with the user's skin or permanently discolor her undergarment. Alternatively, the article may delaminate or tear upon removal if the adhesive has a bond strength to the undergarment greater than the integrity of the article itself. This presents difficult or unsanitary removal and disposal issues of the portions left in the undergarment.

Positioning adhesive can also exacerbate a common consumer complaint referred to as "bunching," which renders absorbent articles uncomfortable and vulnerable to increased probability of peripheral leakage. The forces created between the article and the user's adjacent body parts create this phenomenon. During the dynamics of bunching, the positioning adhesive can adhere to itself creating a permanent crease or fold.

To eliminate positioning adhesives and release sheets altogether, absorbent articles have been designed having high coefficient of friction backsheets. U.S. Pat. No. 5,011,480 discloses such an article. A high coefficient of friction backsheet is a useful means for maintaining the article's position in the user's undergarment when the undergarment is next to the body, which applies a normal force to the article. When the user's undergarment is away from her body, little to no normal forces are exerted on the article, and the frictional characteristics of the backsheet provide minimal resistance to movement of the article. This allows the article to become shifted or separated from the undergarment when the user urinates or initiates usage of the article for the first time. Shifting can create comfort problems and positioning that is less than optimal for absorbing exudates. Separation may also result in article contamination, requiring the user to discard the article.

SUMMARY OF THE INVENTION

The present invention provides an absorbent article comprising a liquid permeable cover; a substantially tack-free, high coefficient of friction backsheet having at least one tape tab affixed to its outwardly disposed surface; and absorbent material. The tape tab has a fixed end, a free end, a first surface, and a second surface opposite the first surface. The second surface of the tape tab has adhesive and release zones thereon. The tape tab can be folded such that the adhesive and release zones face one another prior to article use. These design features eliminate the need for any release sheet or release coating on a wrapper, and also minimize the use of positioning adhesive. The tape tab comprises a minimum amount of adhesive sufficient to maintain the position of the article when a user's undergarments are away from her body. When the undergarments are near her body, the high coefficient of friction backsheet acts as the predominant means for maintaining the position of the article. The tape tab also provides a hygienic and convenient means of placing and removing the article, eliminating or reducing the need for the consumer to touch any portion of the article that will be used to absorb exudates.

The present invention also provides the above absorbent article in a wrapped configuration wherein a portion of the tape tab extends external to the wrapper, allowing the user to open the wrapped product and separate the article from the wrapper using the tape tab.

DETAILED DESCRIPTION OF THE PREFERRED EMBODIMENTS

The present invention provides an absorbent article for managing bodily fluids, comprising a high coefficient of friction ("COF") backsheet and at least one tape tab extending therefrom. The tape tab comprises a minimum amount of pressure sensitive adhesive sufficient to maintain the position of the article when a user's undergarments are away from her body. When the undergarments are near her body, the high COF backsheet acts as the predominant means for maintaining the position of the article due to normal forces exerted by the user's body and undergarments. Throughout this section like elements share like numerical designations.

Figure 1:
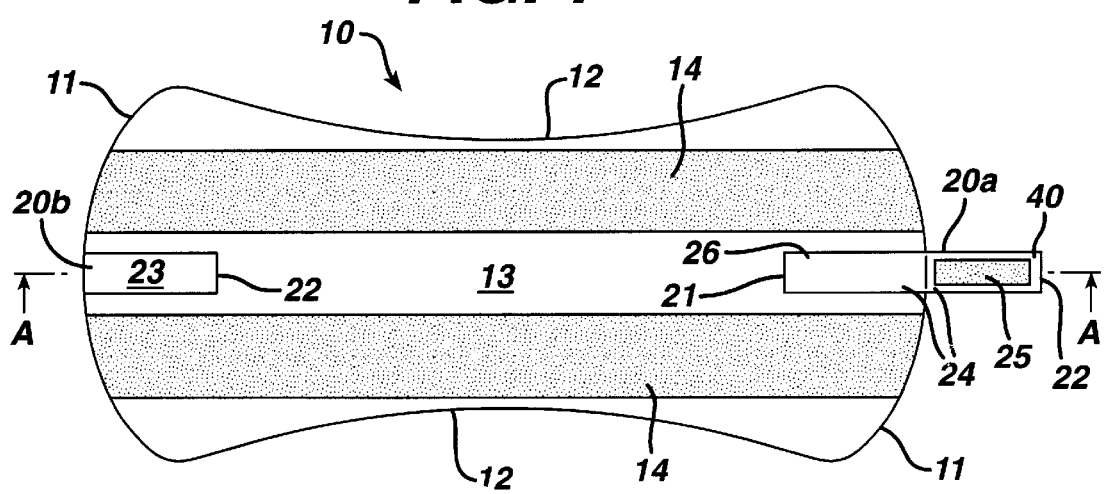
FIG. 1 is a plan view illustrating the backsheet of an article of the present invention comprising two tape tabs, wherein one of the tape tabs is in an extended position, and the second tape tab is folded upon itself.
Figure 2:
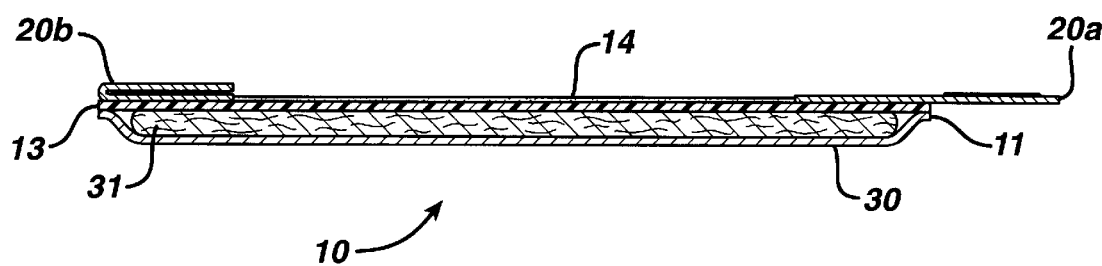
FIG. 2 is a cross-sectional view taken along line A—A in FIG. 1.

Referring to FIGS. 1 and 2, in a preferred embodiment, absorbent article 10 comprises transverse ends 11, longitudinal sides 12, a substantially tack-free, high COF backsheet 13, and two tape tabs 20a and 20b (collectively referred to as "20"). The high COF backsheet is depicted in all of the figures in a preferred embodiment as a substrate having a coating 14 applied thereon (described in greater detail below).

The two tape tabs 20 each have a fixed end 21, free end 22, first surface 23, and a second surface 24 opposite the first surface 23. Each second surface 24 has an adhesive zone 25 and release zone 26 thereon. Tape tab 20a is depicted in an extended position, ready to be attached to the user's undergarments. Tape tab 20b is in a folded configuration such that the adhesive zone 25 and the release zone 26 are in contact. Prior to use, the tape tabs will be configured in the latter manner, leaving no portion of the adhesive zones exposed. This eliminates the requirement of a separate release sheet to protect the adhesive on the tape tabs, as used in many commercial products.

The tape tabs 20 may be manufactured from a number of materials, including fibrous wovens, fibrous nonwovens, polymeric films, paper, and combinations thereof. Preferably, the tape tabs are manufactured from olefinic films, such as polypropylene and polyethylene films, or polyester films. Tape tabs useful for the present invention are commercially available from 3M and Avery Denison.

Although the tape tabs 20 are shown in the figures as generally rectangular, other geometries suitable for use include ovals, circles, and squares. Asymmetrical geometries, such as triangles, may be used as well. The tape tabs 20 typically range in size, having a length from about ½ inch to about 4 inches, a width from about ¼ inch to about 1½ inches, and a caliper of from about 0.001 to about 0.040 inches.

The tape tabs may be attached to the backsheet via the fixed end, as well as optionally a portion of the first surface, by any techniques known to a person having ordinary skill in the art. Particularly useful techniques include heat sealing and adhesives.

Adhesive zones 25 and release zones 26 are located on portions of the tape tab second surface 24. Preferably, the adhesive zones 25 and the release zones 26 are formed from coatings on the second surface. The adhesive and release zones may each consist of a single continuous area, or alternatively, a plurality of areas arranged in a pattern. FIG. 1 depicts the adhesive zone proximal the tape tab free end 22 and the release zone proximal the tape tab fixed end 21. A small area 40 adjacent the free end 22 is uncoated to facilitate opening of the tape tab, transitioning it from a folded configuration to an extended one. The uncoated area should be minimized however to reduce any tendencies for the free end to lift up during use, increasing the potential for user discomfort.

Adhesive zone 25 may comprise any known pressure sensitive adhesives. In a preferred embodiment, the adhesive zone 25 is a continuous extrusion coated area comprising a styrenic block copolymer. Suitable materials for the release zone 26 include, but are not limited to, wax and silicone. Extrusion and printing techniques can be used for coating the tape tabs.

Figure 3:
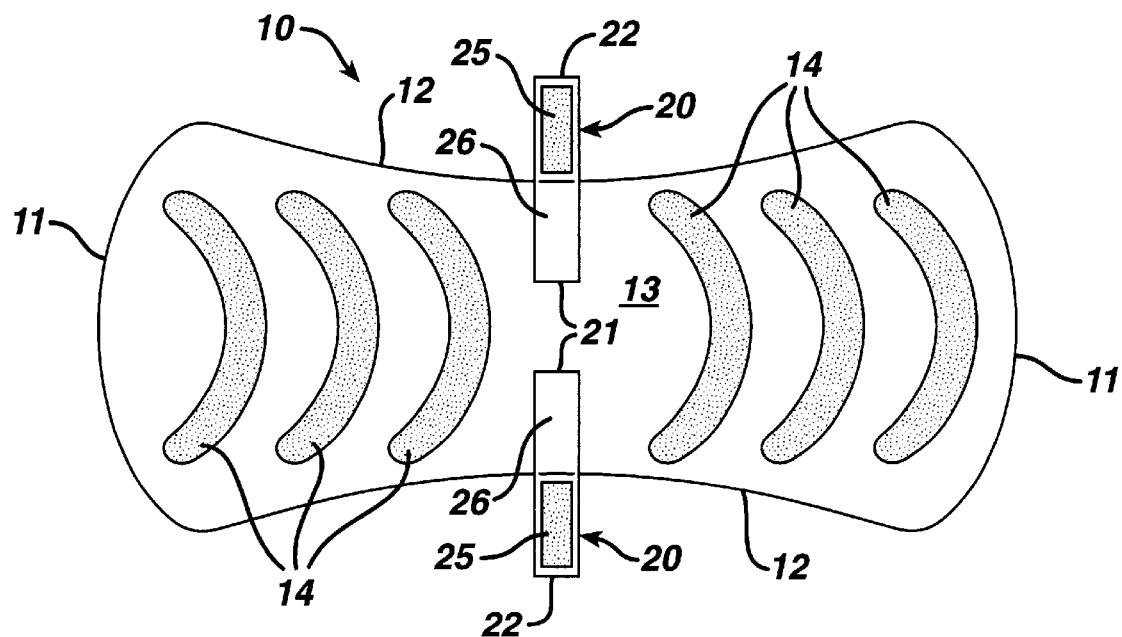
FIG. 3 is a plan view illustrating the backsheet portion of an article of the present invention comprising two tape tabs extending from longitudinal sides of the article.

FIGS. 1 and 2 depict the absorbent article 10 in a preferred embodiment, wherein the tape tabs 20 are proximal the transverse ends 11, and extend in a direction substantially parallel to the longitudinal sides 12. In an alternative embodiment, as shown in FIG. 3, two tape tabs are proximal the longitudinal sides 12, and are configured to extend in a direction substantially parallel to the transverse ends 11. The tape tabs as shown in FIG. 3 may be wrapped around the crotch portion of a user's undergarment and either adhered to one another or the outwardly disposed surface of the undergarment.

Figure 4:
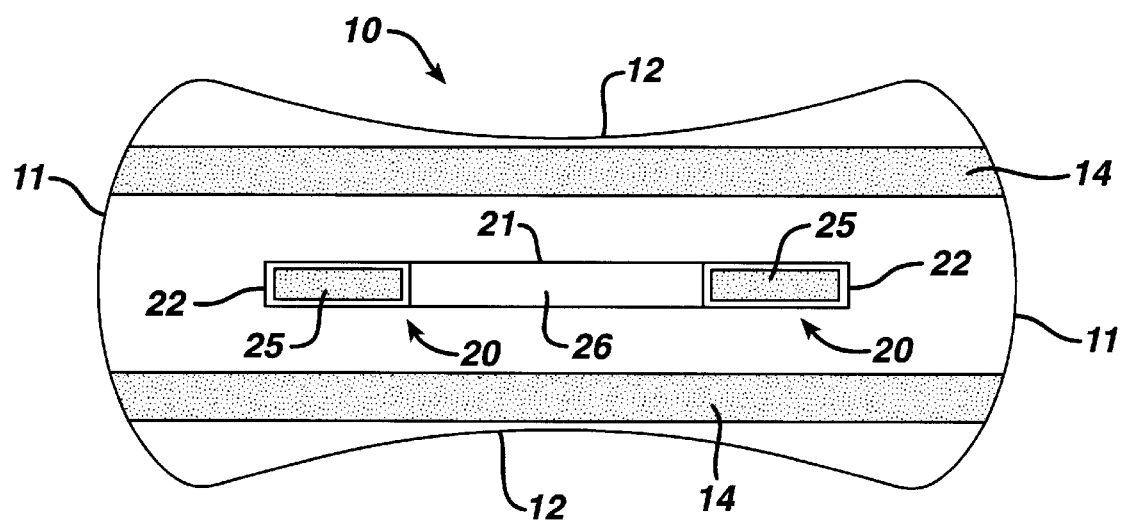
FIG. 4 is a plan view illustrating the backsheet of an article of the present invention comprising two tape tabs maintained within the periphery of the article.

Referring now to FIG. 4, another embodiment of the present invention employs tape tabs 20, which at their fullest extension, are maintained within the periphery of the article 10. This tape tab positioning eliminates contact with the user's body, thereby minimizing any potential discomfort due to the tape tabs lifting and/or chaffing during movement.

In configurations wherein multiple tape tabs are in close proximity to one another, such as those illustrated in FIGS. 3 and 4, the fixed end 21 of the tape tabs 20 may be a continuous strip of material, having two free ends 22. The definition of "continuous" herein includes both two separate elements abutted and affixed, as well as manufactured as a single element.

Tape tabs in numbers greater than two, extending from multiple peripheral points, both parallel and angular in relation to the transverse ends and longitudinal sides, are also contemplated within the scope of the present invention. However, the purpose of the tape tabs 20 is to provide only a temporary anchor of the article to the user's undergarments, during times when her undergarments are away from her body, such as prior to initial article use and during urination. When the undergarments are near her body, the substantially tack-free, high COF backsheet 13 acts as the predominant means for maintaining the position of the article. "Substantially tack-free" is defined herein as yielding a value of less than 100 grams when tested on an inverted probe tester such as the Probe Tack Tester, model number 80-02, available from Testing Machines Incorporated of Mineola, Long Island, N.Y., in conjunction with the standard test method ASTM D2979-95.

The backsheet 13 preferably has a static COF greater than about 1.0, and a dynamic COF greater than about 0.8, as measured by standard test method ASTM D-1894. Although a range of materials may be used as the substrate in ASTM D 1894, cotton is preferred. Specifically, a single knit fabric comprising 30/1 combed and unwaxed 100% cotton at a 162 draw factor; the cotton fibers undergoing a chlorine bleach finishing process.

Backsheet 13 may be a substrate, such as a nonwoven, polymeric film, microporous film, or the like, comprising a substantially tack-free, high COF coating thereon. Such coating preferably has a glass transition temperature (Tg) of less than −15 degrees Celsius. The Tg is the temperature where the maximum loss tangent (Tan δ or G"/G') occurs when dynamic modulus is measured as a function of temperature using a dynamic mechanical spectrometer, such as the Rheometrics RDAII, available from Rheometrics, Inc., Piscatoway, N.J. The coating also preferably has a shear storage modulus (G'), in the temperature range of about −40 to about 50 degrees Celsius (the temperature range of application), of greater than $1 \times 10^5$ dynes per square centimeter. This combination of high COF and modulus, and low Tg and tack provide a backsheet that conforms well to the area to which it is applied, exhibits little or no shifting or bunching during use, and is readily removable for disposal.

Suitable materials for the substantially tack-free, high COF coating are commercially available and include, but are not limited to adhesives 195-338 from ATO-Findley and 34-3396 from National Starch and Chemical. The coating may be applied as hot melts. Preferably, the coat weight of the coating is from about 10 to about 100 milligrams per square inch. The coating may be applied substantially covering the backsheet substrate's outwardly disposed surface, or alternatively in a pattern, such as seen in the figures. In one embodiment of the present invention, the coating may be applied using a hot melt foam adhesive applicator such as the FOAMMELT or FOAMMIX applicator from the Nordson Corporation of Amherst, Ohio.

Another embodiment of the present invention includes the backsheet 13 as a substrate comprising flocked fibers. Methods of flocking fibers are known in the art of fabric manufacture. See for example, U.S. Pat. Nos. 2,257,501; 2,691,611; 3,436,442; and 3,672,929. A representative, non-limiting list of suitable fibers includes rayon, polyester, superabsorbent, nylon, polyvinyl alcohol, and acrylics. Preferred fibers include 6 to 15 denier polyester fibers, such as available from DuPont Company; and superabsorbent polymer fibers, such as available from Technical Absorbents Limited and CAMELOT. In should be appreciated to one skilled in the art that a blend of different fiber types may be used on the backsheet 13.

The high COF backsheet 13 may also be constructed as a single component layer, such as from natural rubbers and olefinic rubbers; and example of which is a polyethylene made by means of a metallocene catalyst.

Referring again to FIG. 2, absorbent article 10 also comprises a liquid permeable cover 30, which is directed towards the body in use. The cover 30 is preferably compliant, soft feeling, and non-irritating to a user's skin. The cover should further exhibit good strikethrough and a reduced tendency to rewet, permitting bodily discharges to rapidly penetrate it and flow toward subsequent underlying layers, while not allowing such discharges to flow back through the cover to the skin of the user.

A suitable cover 30 may be manufactured from a wide range of materials including, but not limited to woven and nonwoven fabrics, apertured formed polymeric films, hydroformed films, porous foams, reticulated foams, reticulated thermoplastic films, and thermoplastic scrims. In addition, the cover may be constructed from a combination of one or more of the above materials, such as a composite layer of nonwoven and apertured formed thermoplastic film.

Apertured films are well suited for the cover 40 because they are pervious to liquids and, if properly apertured (including tapering), have a reduced tendency to allow liquids to pass back through and rewet the user's skin. Useful films are disclosed in the following U.S. Pat. Nos. 3,929,135; 4,324,426; 4,342,314; 4,463,045; and 5,006,394.

Absorbent article 10 further comprises absorbent material 31 for managing fluid uptake and retention. A representative, non-limiting list of absorbent materials useful in the present invention includes natural cellulosics, such as cotton and wood pulp; regenerated cellulosics, such as rayon and cellulose acetate; peat moss; hydrogel-forming polymers in the form of fibers or particles, commonly referred to as "superabsorbents," and the like. One of ordinary skill in the art would readily appreciate that a blend of two or more types of absorbent materials may be used to optimize the performance of absorbent articles used in varying conditions. The absorbent material may be uniformly dispersed, or may alternatively be placed in discrete patterns, or in gradients.

FIG. 2 depicts absorbent material 31 as an absorbent core, i.e., a distinct layer intermediate the liquid permeable cover 30 and backsheet 13. Alternatively, the liquid permeable cover 30 or backsheet 13 may comprise absorbent material within its structure, or on one or both of its surfaces, as a composite structure.

In a core configuration, the absorbent core may have a blend of absorbent materials and thermoplastic fibers, for example to provide structural integrity to the formed structure or for heat sealability to additional layers, such as a barrier layer film. Useful thermoplastic fibers are polyolefins, such as polypropylene and polyethylene fibers. The thermoplastic fibers may be bi-component or multi-component fibers having a first component having a first melting temperature and two or more additional components having melting temperatures different from that of the first component. Bi-component fibers are typically configured sheath-core or side-by-side. Suitable bi-component fibers include polyester/polyethylene and polypropylene/polyethylene An example of a composite structure is a layered nonwoven, comprising a first layer of thermoplastic fibers, a second layer blend of thermoplastic fibers and absorbent fibers, and a third layer identical to the first. The three layers are then bonded through application of heat at a temperature sufficient to induce flow of the thermoplastic material, such as via a heated calandering roll or forced hot air.

The individual layers of the present invention, cover 30, backsheet 13, and absorbent material 31 (if separate and distinct), may employ any known assembly techniques for adhering adjacent layers together. A representative, non-limiting list of assembly techniques and materials, includes adhesives, heat seal, ultrasonic welding, solvent welding, and mechanical fastening. Preferably, construction adhesives are used to laminate individual elements to one another. Suitable construction adhesives are disclosed in the following U.S. Pat. Nos. 4,526,577; 5,149,741; and 5,057,571. The construction adhesives may be modified to be absorbent by incorporating absorbing polymer into their formulations.

Figure 5:
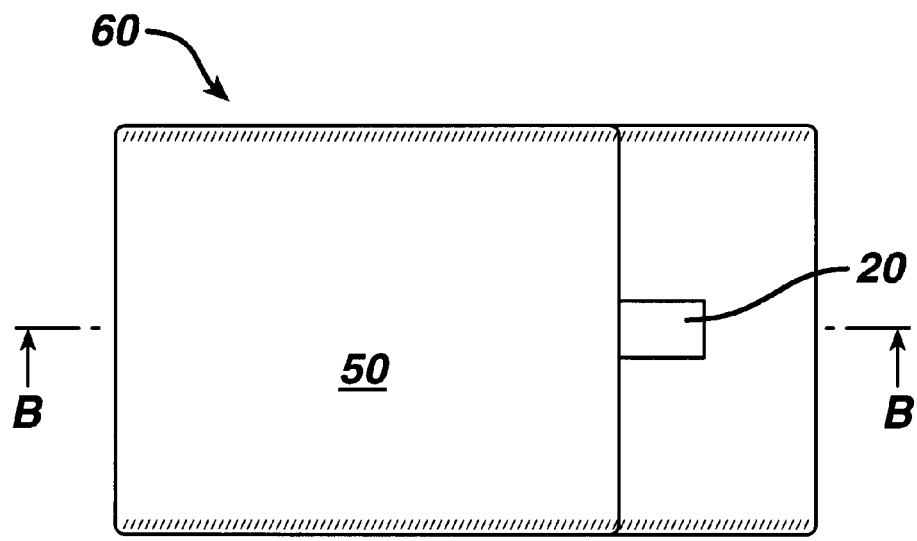
FIG. 5 is a plan view of an individually folded and wrapped product of the present invention comprising a tape tab, which extends externally of the wrapper.
Figure 6:
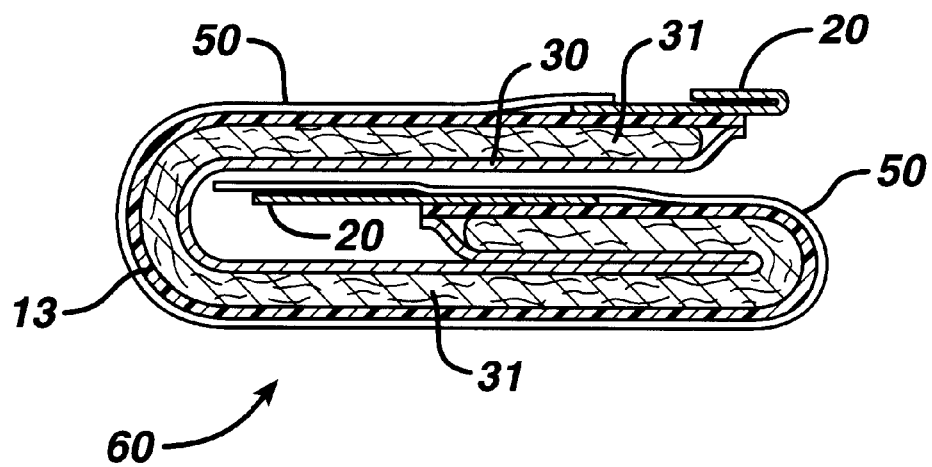
FIG. 6 is a cross-sectional view taken along line B—B in FIG. 5

Now referring to FIGS. 5 and 6, the absorbent articles of the present invention may be individually wrapped in a flat, folded, or rolled manner for easy portability. In a preferred embodiment, at least one tape tab 20 extends external to a wrapper 50. This configuration allows a user to open the individually wrapped product 60 and separate the article 10 from the wrapper 50. The wrapper 50 may optionally employ features that render it useful as a disposal means for soiled articles. The wrapper 50 may be constructed from any materials known in the art for such packaging purposes. In a preferred embodiment, the wrapper is made from paper or a polymeric film, such as polypropylene.

The absorbent articles of the present invention may be of any shape suitable for placement against a user's perineum and the surrounding areas. Shapes include rectangular, oval, dogbone, peanut shape, and the like. Asymmetry with respect to the transverse ends may a useful shape as well, such as for use in "thong-type" undergarments.

To use an absorbent article of the present invention, the user first removes an it from any exterior packaging, for example a flexible bag or cardboard carton, and any individual wrapping as well. The tape tab will be in a folded configuration such that the adhesive is in contact with the release zones, that is, the adhesive is not yet exposed. The user then must expose the adhesive on the tape tab, such as by unfolding to an extended position. The user can then adhere the tape tab to her undergarments, for maintaining the article's placement prior to, and while she is pulling her undergarments close to her body. During removal of the article from undergarments, the tape tab provides additional advantages. A user may grasp the tape tab itself for removing the article as an alternative to grasping a portion of the soiled article. In addition, the soiled article may be folded or rolled up, and then held in that configuration with the tape tab, for convenient and discreet disposal.

The disclosures of all patents, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent article, comprising:
   (a) a liquid permeable cover;
   (b) a substantially tack-free, high coefficient of friction backsheet having at least one tape tab affixed to its outwardly disposed surface; and
   (c) an absorbent material;
wherein the tape tab has a fixed end, a free end, a first surface, and a second surface opposite the first surface having adhesive and release zones thereon, the backsheet comprises a substrate having a substantially tack-free, high coefficient of friction coating on its outwardly disposed surface, and the coat weight of the high coefficient of friction coating is from about 10 to about 100 milligrams per square inch.

2. An absorbent article, comprising:
   (a) a liquid permeable cover;
   (b) a substantially tack-free, high coefficient of friction backsheet having at least one tape tab affixed to its outwardly disposed surface; and
   (c) an absorbent material;
wherein the tape tab has a fixed end, a free end, a first surface, and a second surface opposite the first surface having adhesive and release zones thereon, the backsheet comprises a substrate having a substantially tack-free, high coefficient of friction coating on its outwardly disposed surface, and wherein the coating has a shear storage modulus of greater than about $1 \times 10^5$ dynes per square centimeter at a temperature of about −40 to about 50 degrees Celsius.

3. An absorbent article, comprising:
   (a) a liquid permeable cover;
   (b) a substantially tack-free, high coefficient of friction backsheet having at least one tape tab affixed to its outwardly disposed surface; and
   (c) an absorbent material;
wherein the tape tab has a fixed end, a free end, a first surface, and a second surface opposite the first surface having adhesive and release zones thereon, the backsheet comprises a substrate having a substantially tack-free, high coefficient of friction coating on its outwardly disposed surface and the coating has a static coefficient of friction of greater than about 1.0 and a dynamic coefficient of friction greater than about 0.8, and the coating has a glass transition temperature of less than about −15 degrees Celsius.

4. An absorbent article, comprising:
   (a) a liquid permeable cover;
   (b) a substantially tack-free, high coefficient of friction backsheet having at least one tape tab affixed to its outwardly disposed surface; and
   (c) an absorbent material;
wherein the tape tab has a fixed end, a free end, a first surface, and a second surface opposite the first surface having adhesive and release zones thereon, wherein the backsheet comprises a substrate having flocked fibers thereon.

5. An individually wrapped product, comprising:
   a. an absorbent article, comprising:
      i) a liquid permeable cover;
      ii) a substantially tack-free, high coefficient of friction backsheet having at least one tape tab affixed to its outwardly disposed surface; and
      iii) an absorbent material;
         wherein the tape tab has a fixed end, a free end, a first surface, and a second surface opposite the first surface having adhesive and release zones thereon; and
   b. a flexible wrapper enveloping the article;
wherein a portion of at least one tape tab extends external to the wrapper, whereby a user may open the individually wrapped product and separate the article from the wrapper using the tape tab.

6. The individually wrapped product of claim 5 wherein the flexible wrapper comprises paper.

7. The individually wrapped product of claim 5 wherein the flexible wrapper is a polymeric film.

* * * * *